United States Patent
Iede

(10) Patent No.: US 9,820,633 B2
(45) Date of Patent: Nov. 21, 2017

(54) FLEXIBLE TUBULAR PORTION OF ENDOSCOPE AND ENDOSCOPE HAVING THIS FLEXIBLE TUBULAR PORTION

(71) Applicant: OLYMPUS CORPORATION, Shibuya-ku, Tokyo (JP)

(72) Inventor: Taro Iede, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 331 days.

(21) Appl. No.: 14/173,192

(22) Filed: Feb. 5, 2014

(65) Prior Publication Data

US 2014/0155697 A1 Jun. 5, 2014

Related U.S. Application Data

(63) Continuation of application No. PCT/JP2012/078374, filed on Nov. 1, 2012.

(30) Foreign Application Priority Data

Nov. 4, 2011 (JP) ................... 2011-242704

(51) Int. Cl.
*A61B 1/00* (2006.01)
*A61B 1/04* (2006.01)
(Continued)

(52) U.S. Cl.
CPC ............ *A61B 1/0055* (2013.01); *A61B 1/005* (2013.01); *A61B 1/0051* (2013.01);
(Continued)

(58) Field of Classification Search
CPC ............ A61B 1/00064; A61B 1/00071; A61B 1/00078; A61B 1/005; A61B 1/0051;
(Continued)

(56) References Cited

U.S. PATENT DOCUMENTS 4,669,172 A * 6/1987 Petruzzi ............... A61B 1/0055
138/131
5,549,542 A * 8/1996 Kovalcheck ......... A61B 1/0052
600/146

(Continued)

FOREIGN PATENT DOCUMENTS

| CN | 1907211 A | 2/2007 |
| CN | 101115432 A | 1/2008 |

(Continued)

OTHER PUBLICATIONS

Chinese Office Action (and English translation thereof) dated May 27, 2015, issued in counterpart Chinese Application No. 201280039719.5.

(Continued)

*Primary Examiner* — Ryan Henderson
(74) *Attorney, Agent, or Firm* — Holtz, Holtz & Volek PC

(57) ABSTRACT

A flexible tubular portion of an endoscope includes a spiral tube portion. The spiral tube portion includes a closely wound portion to at least a part of which an initial tension is applied, and a sparsely wound portion provided at least at one end of the closely wound portion.

9 Claims, 9 Drawing Sheets

(51) Int. Cl.
*A61M 25/00* (2006.01)
*A61B 1/005* (2006.01)
*A61B 17/00* (2006.01)
*G02B 23/24* (2006.01)

(52) U.S. Cl.
CPC ........ *A61B 1/0057* (2013.01); *A61B 1/00064* (2013.01); *A61B 1/00071* (2013.01); *A61B 2017/003* (2013.01); *A61B 2017/00305* (2013.01); *A61B 2017/00309* (2013.01); *G02B 23/2476* (2013.01)

(58) Field of Classification Search
CPC ... A61B 1/0052; A61B 1/0053; A61B 1/0055; A61B 1/0056; A61B 1/0057; A61B 1/0058; A61B 1/008; A61B 1/01; A61B 2017/003; A61B 2017/00305; A61B 2017/00309; A61B 2017/00314; A61B 2017/00318; A61B 2017/00323; A61B 2017/00327; A61B 2017/00331
USPC ......... 600/128, 130, 139–144; 604/523–528; 138/118, 121–136, 144, 176
See application file for complete search history.

(56) References Cited

U.S. PATENT DOCUMENTS

| | | | |
|---|---|---|---|
| 8,317,684 B2 | 11/2012 | Matsuo et al. | |
| 2006/0111617 A1* | 5/2006 | Wimmer | A61B 1/00078 600/146 |
| 2007/0233040 A1* | 10/2007 | Macnamara | A61B 1/00071 604/523 |
| 2007/0233043 A1* | 10/2007 | Dayton | A61B 1/00071 604/526 |
| 2010/0168519 A1 | 7/2010 | Matsuo | |

FOREIGN PATENT DOCUMENTS

| | | | | |
|---|---|---|---|---|
| CN | 101467865 A | | 7/2009 | |
| JP | 58-103431 A | | 6/1983 | |
| JP | 63281618 A | * | 11/1988 | ............... A61B 1/01 |
| JP | DE 4102211 A1 | * | 8/1991 | .......... A61B 1/0055 |
| JP | 5-95895 A | | 4/1993 | |
| JP | 7-213481 A | | 8/1995 | |
| JP | 11-262470 A | | 9/1999 | |
| JP | 11-285469 A | | 10/1999 | |
| JP | 2010-104668 A | | 5/2010 | |

OTHER PUBLICATIONS

Japanese Office Action (and English translation thereof) dated Jul. 28, 2015, issued in counterpart Japanese Application No. 2011-242704.
Chinese Office Action (and English translation thereof) dated Dec. 3, 2015, issued in Chinese Application No. 201280039719.5.
International Preliminary Report on Patentability (IPRP) including Written Opinion dated May 15, 2014 in parent International Application No. PCT/JP2012/078374.
International Search Report (ISR) dated Dec. 18, 2012 (and English translation thereof) issued in counterpart International Application No. PCT/JP2012/078374.

* cited by examiner

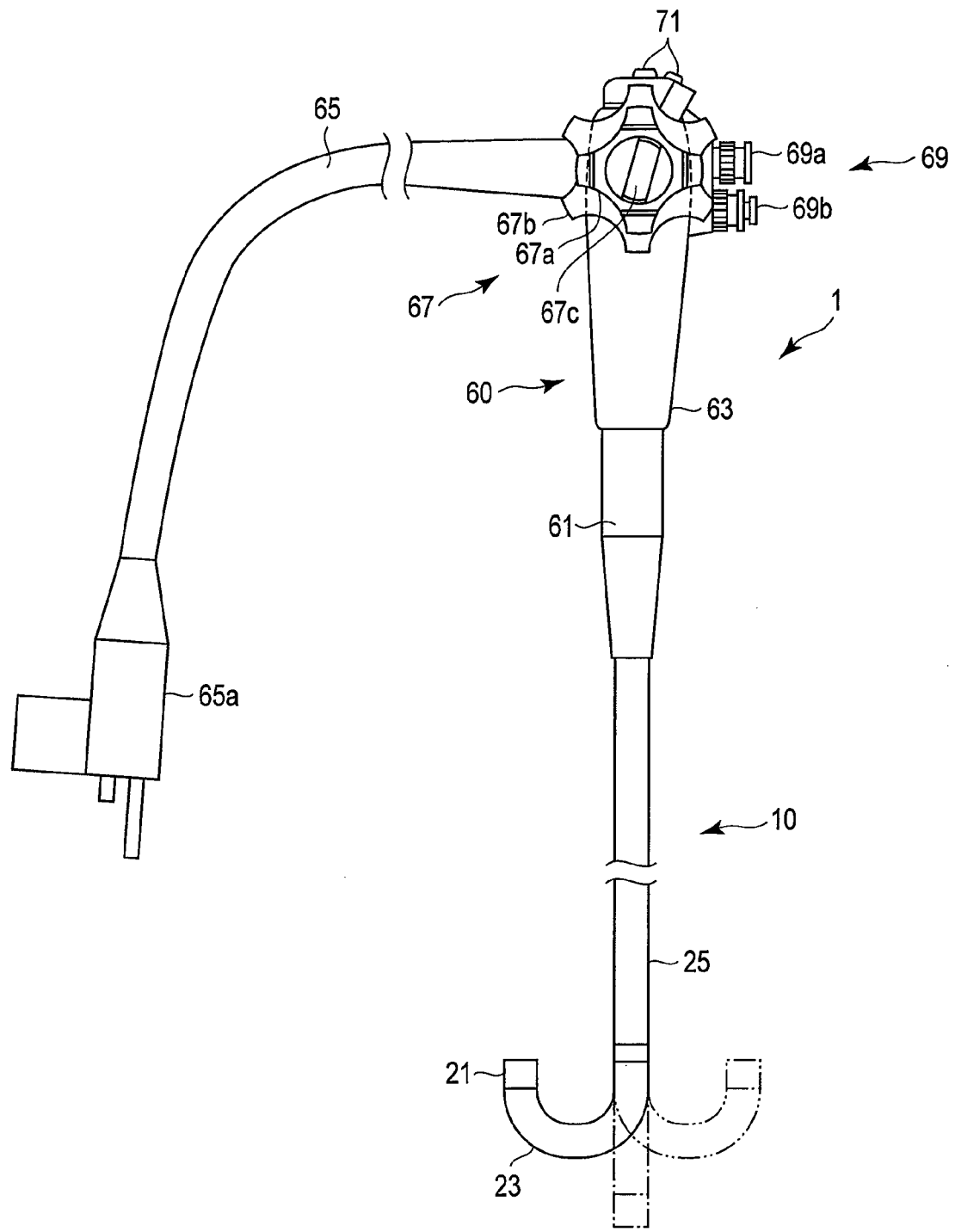
F I G. 1

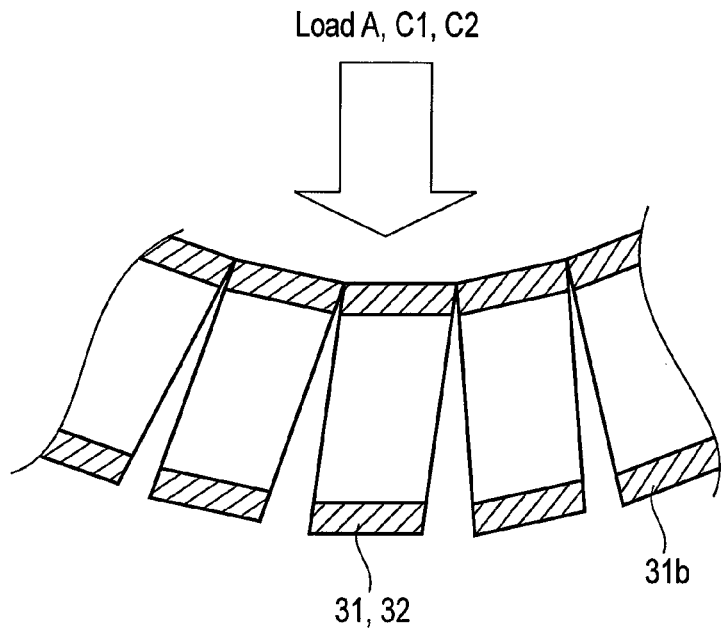
F I G. 3D
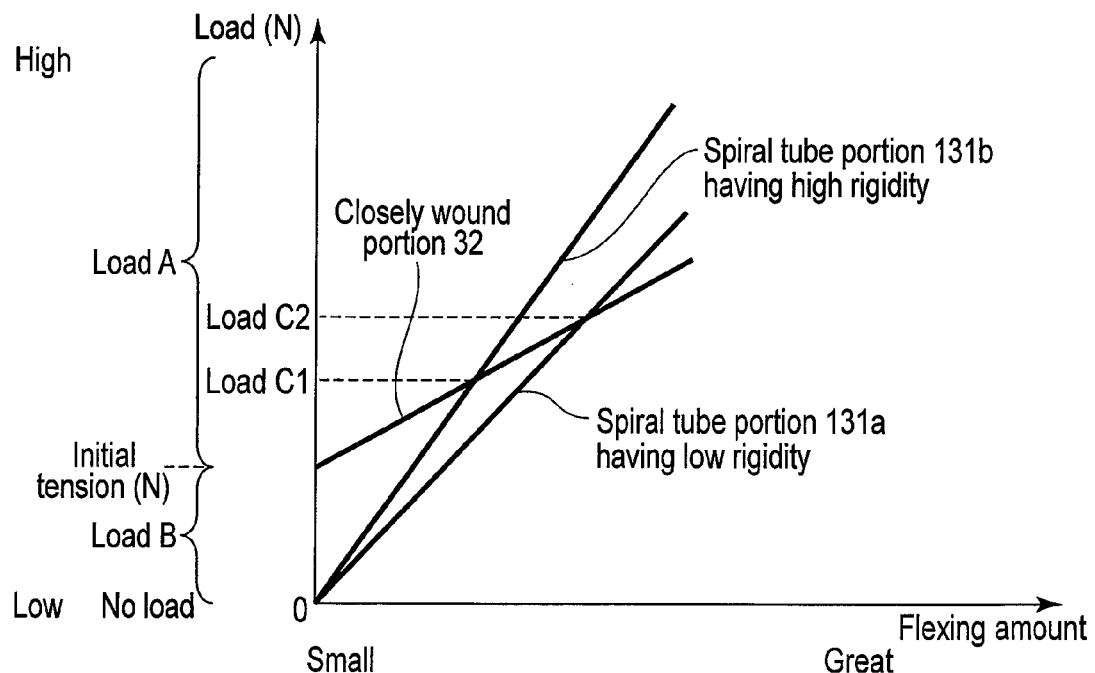
F I G. 4

FLEXIBLE TUBULAR PORTION OF ENDOSCOPE AND ENDOSCOPE HAVING THIS FLEXIBLE TUBULAR PORTION

CROSS-REFERENCE TO RELATED APPLICATIONS

This application is a Continuation Application of PCT Application No. PCT/JP2012/078374, filed Nov. 1, 2012 and based upon and claiming the benefit of priority from prior Japanese Patent Application No. 2011-242704, filed Nov. 4, 2011, the entire contents of all of which are incorporated herein by reference.

BACKGROUND OF THE INVENTION

1. Field of the Invention

The present invention relates to a flexible tubular portion of an endoscope, and an endoscope having the flexible tubular portion.

2. Description of the Related Art

In general, an endoscope has a flexible tubular portion. A flexible tubular portion is disclosed in, for example, Jpn. Pat. Appln. KOKAI Publication No. 11-285469. The flexible tubular portion includes, for example, a metallic spiral tube portion, a mesh tube portion which is provided outside the spiral tube portion and which covers the spiral tube portion, and an outer tube which is provided outside the mesh tube portion and which covers the mesh tube portion. The mesh tube portion is stacked on the spiral tube portion, and the outer tube is stacked on the mesh tube portion. Thus, the flexible tubular portion has a three-layer structure.

The flexible tubular portion has a flexibility, and is therefore flexed, for example, when a load is applied thereto. In this case, the load is proportional to the flexing amount (deformation amount), and the flexing amount is greater when the load is higher. This load is, for example, an external pressure received from the intestines when the flexible tubular portion is inserted into the large intestine and abuts on a flection such as the sigmoid colon in the large intestine.

BRIEF SUMMARY OF THE INVENTION

According to one aspect of a flexible tubular portion of an endoscope of the present invention, there is provided the flexible tubular portion of an endoscope including a spiral tube portion, wherein the spiral tube portion comprises a closely wound portion to at least a part of which an initial tension is applied, and a sparsely wound portion provided at least at one end of the closely wound portion.

According to one aspect of the present invention, there is provided an endoscope comprising the above-mentioned flexible tubular portion of the endoscope.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram of an endoscope according to the present invention;

FIG. 3D is a diagram showing how the closely wound portion is flexed by the application of a load equal to or more than the initial tension from the state shown in FIG. 3A;

FIG. 4 is a graph showing the relation between the load and the flexing amount in the closely wound portion and the general spiral tube portion;

DETAILED DESCRIPTION OF THE INVENTION

Figure 2:
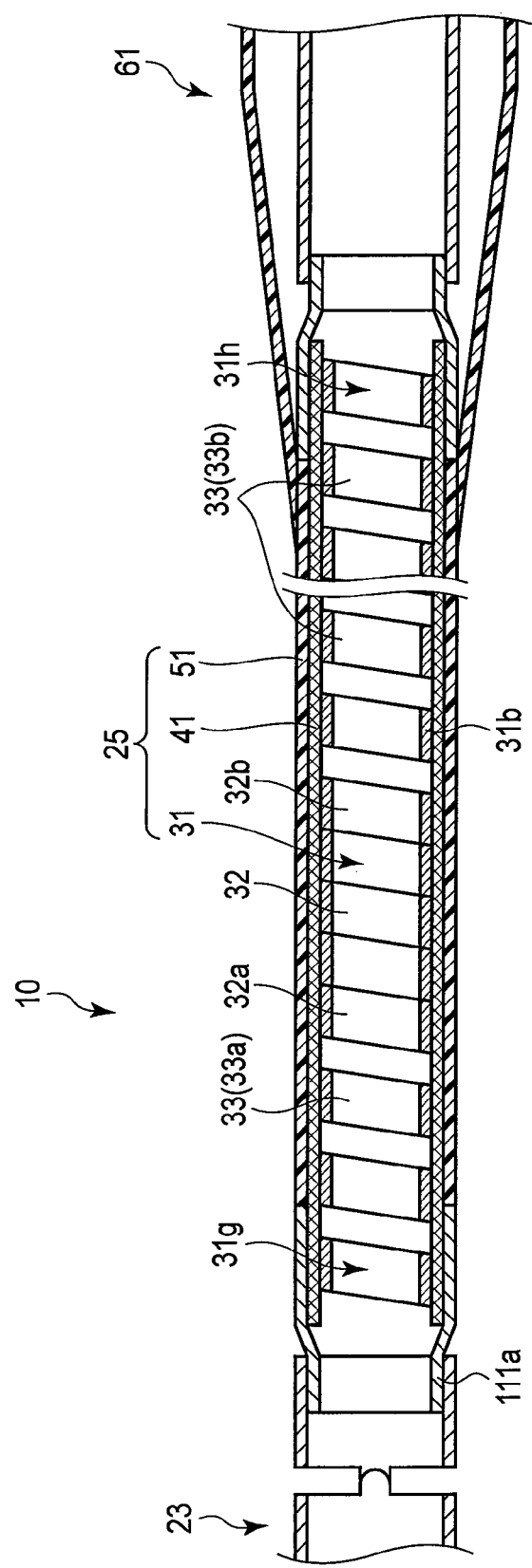
FIG. 2 is a diagram showing a three-layer structure of a flexible tubular portion.

Hereinafter, embodiments of the present invention will be described in detail with reference to the drawings.

First Embodiment

[Configuration]

A first embodiment is described with reference to FIG. 1, FIG. 2, FIG. 3A, FIG. 3B, FIG. 3C, FIG. 3D, FIG. 4, FIG. 5A, and FIG. 5B.

[Endoscope 1]

As shown in FIG. 1, an endoscope 1 has an elongated insertion portion 10 to be inserted into, for example, a body cavity of a patient, and an operation portion 60 which is coupled to a proximal end portion of the insertion portion 10 and which operates the endoscope 1.

[Insertion Portion 10]

The insertion portion 10 has a distal hard portion 21, a bending portion 23, and a flexible tubular portion 25 in order from a distal end portion side of the insertion portion 10 to the proximal end portion side of the insertion portion 10. A proximal end portion of the distal hard portion 21 is coupled to a distal end portion of the bending portion 23. A proximal end portion of the bending portion 23 is coupled to a distal end portion of the flexible tubular portion 25.

The distal hard portion 21 is the distal end portion of the insertion portion 10, and is hard and unbendable.

The bending portion 23 is bent in a desired direction, for example, in vertical and horizontal directions by the operation of a bending operation portion 67 described later. When the bending portion 23 is bent, a position and direction of the distal hard portion 21 change, an observation target is illuminated by illumination light, and the observation target is caught in an observation field.

The flexible tubular portion 25 has desired flexibility. Thus, the flexible tubular portion 25 is flexed by external force. The flexible tubular portion 25 is a tubular member extending from a later-described main body portion 61 in the operation portion 60. The structure of the flexible tubular portion 25 will be described later.

[Operation Portion 60]

The operation portion 60 has the main body portion 61 from which the flexible tubular portion 25 extends, a grasp portion 63 which is coupled to a proximal end portion of the main body portion 61 and which is grasped by an operator who operates the endoscope 1, and a universal cord 65 connected to the grasp portion 63.

[Grasp Portion 63]

The grasp portion 63 has the bending operation portion 67 which is operated to bend the bending portion 23. The bending operation portion 67 has a horizontal bending operation knob 67a which is operated to horizontally bend the bending portion 23, and a vertical bending operation knob 67b which is operated to vertically bend the bending portion 23, and a fixing knob 67c which fixes the position of the bent bending portion 23.

The grasp portion 63 also has a switch portion 69. The switch portion 69 has a suction switch 69a and an air/water supply switch 69b. The switch portion 69 is operated by the hand of the operator when the grasp portion 63 is grasped by the operator. The suction switch 69a is operated when the endoscope 1 sucks, for example, mucus or fluid from an unshown suction opening portion provided in the distal hard portion 21 via an unshown suction channel. The air/water supply switch 69b is operated when the fluid is supplied from an unshown air/water supply channel to secure an observation field of an unshown imaging unit in the distal hard portion 21. The fluid includes liquid and gases.

The grasp portion 63 has various buttons 71 for endoscopic photography.

[Universal Cord 65]

The universal cord 65 has a connection portion 65a to be connected to an unshown video processor or a light source device.

[Flexible Tubular Portion 25]

Now, the structure of the flexible tubular portion 25 is described with reference to FIG. 1 and FIG. 2.

The flexible tubular portion 25 has, for example, a hollow shape. More specifically, as shown in FIG. 2, the flexible tubular portion 25 has, for example, a spiral tube portion 31, a mesh tube portion 41 which is provided outside the spiral tube portion 31 and which covers the outer circumferential surface of the spiral tube portion 31, and an outer tube 51 which is provided outside the mesh tube portion 41 and which covers the outer circumferential surface of the mesh tube portion 41. The mesh tube portion 41 is stacked on the spiral tube portion 31, and the outer tube 51 is stacked on the mesh tube portion 41.

Thus, the flexible tubular portion 25 is composed of the spiral tube portion 31, the mesh tube portion 41, and the outer tube 51 so that the flexible tubular portion 25 has a three-layer structure. A diameter of the flexible tubular portion 25 is, for example, 12 mm.

[Spiral Tube Portion 31]

The spiral tube portion 31 according to the present embodiment is a spiral elastic tube member having resilient force. This resilient force includes, for example, a rebound property, impact resilience, hysteresis, and spring characteristics, and has the property of restoring the bent spiral tube portion 31 to a substantially straight state. The spiral tube portion 31 is formed into the shape of a coil pipe. As shown in FIG. 2 and FIG. 3A, the spiral tube portion 31 integrally has a closely wound portion 32 to which an initial tension is applied, and a sparsely wound portions 33 provided in both end of the closely wound portion 32. Since the spiral tube portion 31 has the resilient force, the closely wound portion 32 is configured as, for example, a closely coil spring, and the sparsely wound portions 33 are configured as, for example, sparsely wound coil springs. The closely wound portion 32 is, for example, a closely wound coil. The sparsely wound portions 33 are, for example, sparsely wound coils. The initial tension is applied along a longitudinal axis direction of the closely wound portion 32.

Figure 3A:
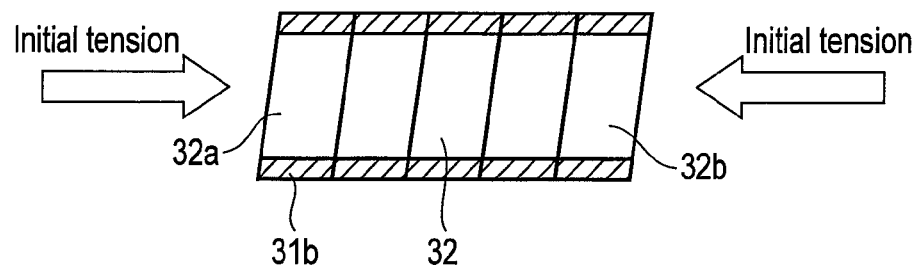
FIG. 3A is a diagram showing a spiral tube portion (closely wound portion) to which an initial tension is applied.

As shown in FIG. 2 and FIG. 3A, the closely wound portion 32 has a distal end portion 32a and a proximal end portion 32b. The distal end portion 32a is connected to one sparsely wound portion 33a, and the proximal end portion 32b is connected to the other sparsely wound portion 33b. Thus, the closely wound portion 32 is held between the sparsely wound portions 33 in a axial direction of the spiral tube portion 31, and is adjoined to the sparsely wound portions 33 at the distal end portion 32a and the proximal end portion 32b. Therefore, in the present embodiment, in the axial direction of the spiral tube portion 31, the spiral tube portion 31 has the sparsely wound portion 33a, the closely wound portion 32, and the sparsely wound portion 33b in order from a distal end portion 31g of the spiral tube portion 31 (the flexible tubular portion 25) to a proximal end portion 31h of the spiral tube portion 31 (the flexible tubular portion 25).

The closely wound portion 32 and the sparsely wound portions 33 are spiral wire rods formed by a spiral wire 31b. The closely wound portion 32 and the sparsely wound portions 33 are formed as one by the same wire 31b.

The closely wound portion 32 is formed so that the wires 31b adjacent in the axial direction of the spiral tube portion 31 are brought into close contact with each other without space therebetween by the above-mentioned initial tension. That is, in the closely wound portion 32, the wires 31b are in close contact with each other in the axial direction of the spiral tube portion 31.

In contrast, in the sparsely wound portion 33 to which the initial tension is not applied, the sparsely wound portion 33 is formed so that the wires 31b are provided apart from each other in the axial direction of the spiral tube portion 31 to have space in the axial direction of the spiral tube portion 31. That is, in the sparsely wound portion 33, the wires 31b are not in close contact with each other in the axial direction of the spiral tube portion 31.

[Initial Tension]

Now, the initial tension is described.

Under no load, the initial tension is the force which works in a direction to bring the wires 31b of the closely wound portion 32 into close contact with each other in the axial direction of the closely wound portion 32. In other words, the initial tension is the force which keeps the closely wound portion 32 straight without flexing even if external force (for example, gravity) is applied to the closely wound portion 32 in a no-load condition. Therefore, when external force is applied to the closely wound portion 32 in the no-load condition, the wires 31b are brought into close contact with each other in the axial direction by the initial tension, and the closely wound portion 32 is not flexed by the initial tension.

This initial tension is applied to the closely wound portion 32 from the side of the distal end portion 32a of the closely wound portion 32 and the side of the proximal end portion 32b of the closely wound portion 32 toward the center of the closely wound portion 32 along the axial direction of the closely wound portion 32 as shown in FIG. 3A when the closely wound portion 32 is formed. For example, the initial tension is applied from the distal end portion 32a to the proximal end portion 32b in the axial direction of the closely wound portion 32. Initial tension A in this case is, for example, $0N < A \leq 25N$. This initial tension of the closely wound portion 32 can be adjusted, for example, by a winding direction in which the wire 31b is spirally wound.

As shown in FIG. 3A, for example, the initial tension is the force which works in a direction to bring the edges of the wires 31b of the closely wound portion 32 into close contact with each other in a central axis direction of the closely wound portion 32. In other words, when a central axis of the closely wound portion 32 is, for example, horizontally placed, the initial tension is the force (preload) which keeps the edges of the wires 31b of the closely wound portion 32 in close contact with each other and keeps the closely wound portion 32 difficult to bend and substantially straight against external force F (e.g., gravity). When the central axis of the closely wound portion 32 is, for example, vertically placed, the initial tension is the force (preload) which keeps the edges of the wires 31b of the closely wound portion 32 in close contact with each other against gravity and keeps no space between the wires 31b.

For example, as shown in FIG. 3A, suppose that the external force F is applied to the central axis of the closely wound portion 32 when the central axis is, for example, horizontally placed. In this case, until the external force F reaches a force that cancels the initial tension, in other words, until the external force F surpasses the initial tension, no space is formed between the wires 31b, and the closely wound portion 32 is not bent. On the other hand, when the external force F applied to the central axis becomes equal to or more than the force that cancels the initial tension as shown in FIG. 3D, in other words, when the external force F surpasses the initial tension, a space is formed between the wires 31b that have been in close contact, and the closely wound portion 32 is bent. Therefore, the flexural rigidity of the spiral tube portion 31 is high because of the initial tension applied to the closely wound portion 32 until the closely wound portion 32 starts bending. When the initial tension is canceled by the external force F and the closely wound portion 32 starts bending, the spiral tube portion 31 bends in accordance with the spring constant of the spiral tube portion 31. Therefore, once the insertion portion 10 is inserted into a body cavity (lumen) such as the large intestine and the closely wound portion 32 starts bending, the flexible tubular portion 25 can be bent as if the closely wound portion 32 were not present.

Figure 3B:
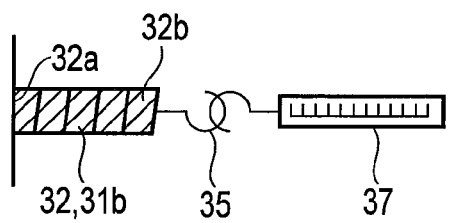
FIG. 3B is a diagram showing how to measure the initial tension.

As shown in FIG. 3B, for example, a hook portion 35 is provided in the proximal end portion 32b of the closely wound portion 32 to measure the initial tension. A measuring instrument 37 such as a digital force gauge is hooked to the hook portion 35. The distal end portion 32a of the closely wound portion 32 is fixed, and the measuring instrument 37 pulls the closely wound portion 32 along the axial direction of the closely wound portion 32 via the hook portion 35. The measuring instrument 37 measures the load when the closely wound portion 32 is pulled and stretched in the axial direction (when the wires 31b are separated). The measured load is the initial tension.

Figure 3C:
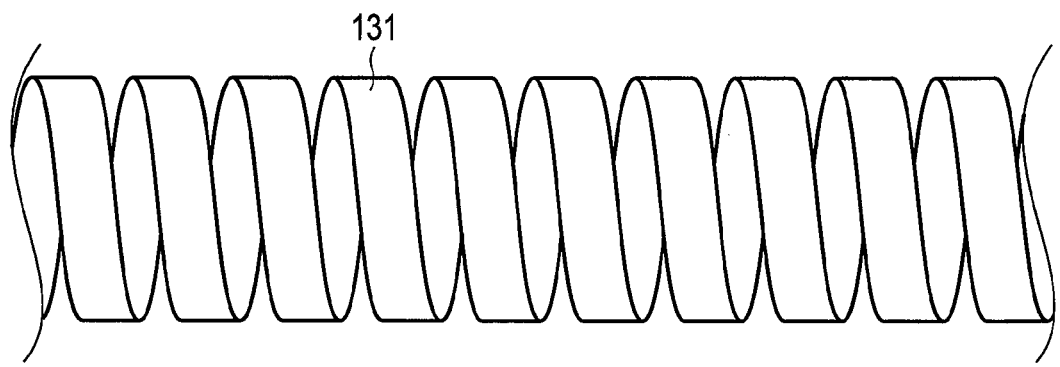
FIG. 3C is a diagram showing a general spiral tube portion which is formed by molding a belt-shaped thin plate material into a spiral shape.

A general spiral tube portion 131 is formed into the shape of a substantially circular tube by molding a belt-shaped thin plate material made of, for example, a stainless steel material into a spiral shape, as shown in FIG. 3C. This spiral tube portion 131 is, for example, a thin metallic spiral tube portion.

The spiral tube portion 131 is flexed by the application of the load in a diametrical direction of the spiral tube portion 131. In this case, in the spiral tube portion 131, the load is proportional to the flexing amount (deformation amount), and the flexing amount is greater when the load is higher. With the same load, the flexing amount is greater when the rigidity of the spiral tube portion 131 is lower. In other words, with the same load, the flexing amount of a spiral tube portion 131a having low rigidity is greater than the flexing amount of a spiral tube portion 131b having high rigidity, as shown in FIG. 4.

As shown in FIG. 3D and FIG. 4, the closely wound portion 32 is flexed for the first time in accordance with the spring constant of the closely wound portion 32 when a load (hereinafter referred to as load A) equal to or more than the initial tension is applied to the closely wound portion 32. This load is, for example, an external pressure received from the intestines when the flexible tubular portion 25 is inserted into the large intestine and abuts on a flection such as the sigmoid colon of the large intestine.

The closely wound portion 32 according to the present embodiment has a spring constant lower than the rigidity of the spiral tube portion 131, and is flexed in accordance with this rigidity.

[Flexibility of Closely Wound Portion 32 and Spiral Tube Portion 131]

Now, the flexing of the closely wound portion 32 and the spiral tube portion 131 is described in detail.

As described above and as shown in FIG. 3A and FIG. 4, the closely wound portion 32 is not flexed by the initial tension in the no-load condition. Moreover, as shown in FIG. 3A and FIG. 4, the wires 31b are brought into close contact by the initial tension, so that the closely wound portion 32 is not flexed even by the application of a load (hereinafter referred to as load B) equal to or less than the initial tension to the closely wound portion 32 in the diametrical direction of the closely wound portion 32. That is, the flexing amount is 0. Thus, the closely wound portion 32 keeps substantially straight in the no-load condition and under the load B.

As shown in FIG. 3D and FIG. 4, the wires 31b are not separated each other and the closely wound portion 32 is flexed for the first time when the load A is applied to the closely wound portion 32 in the diametrical direction of the closely wound portion 32. That is, the flexing amount is equal to or more than 0. In other words, the closely wound portion 32 is not flexed by the initial tension unless the load A is applied to the closely wound portion 32.

When the load A is applied to the closely wound portion 32, the closely wound portion 32 is flexed in proportion to the spring constant of the closely wound portion 32 lower than the rigidity of the spiral tube portion 131, as shown in FIG. 4.

When the load is equal to or more than predetermined loads (hereinafter referred to as loads C1 and C2) within the load A, the closely wound portion 32 is flexed more than the spiral tube portion 131 shown in FIG. 3C under the same load. The load C2 is higher than the load C1.

For example, when a load equal to or more than the load C1 is applied to the closely wound portion 32 and the spiral tube portion 131b having high rigidity, the closely wound portion 32 is flexed more than the spiral tube portion 131b having high rigidity under the same load. In other words, a load equal to or more than the load C1 is applied to the closely wound portion 32 and the spiral tube portion 131b having high rigidity, and the flexing amount of the closely wound portion 32 is the same as the flexing amount of the spiral tube portion 131b having high rigidity, in which case the load applied to the closely wound portion 32 is lower than the load applied to the spiral tube portion 131b having high rigidity.

When, for example, a load equal to or more than the load C2 is applied to the closely wound portion 32 and the spiral tube portion 131a having low rigidity, the closely wound portion 32 is flexed more than the spiral tube portion 131a having low rigidity under the same load. In other words, a load equal to or more than the load C2 is applied to the closely wound portion 32 and the spiral tube portion 131a having low rigidity, and the flexing amount of the closely wound portion 32 is the same as the flexing amount of the spiral tube portion 131a having low rigidity, in which case the load applied to the closely wound portion 32 is lower than the load applied to the spiral tube portion 131a having low rigidity.

In the present embodiment, when a load equal to or more than the initial tension and equal to or less than the load C2 is applied to the closely wound portion 32, an operating force amount at the hand side is transmitted to the distal end portion side of the flexible tubular portion 25, and the closely wound portion 32 is slightly flexed to a degree enough for the flexible tubular portion 25 to be easily inserted into the body cavity.

Although the flexing of the closely wound portion 32 has been described above, the same also applies to the flexing of the flexible tubular portion 25 having the closely wound portion 32.

The closely wound portion 32 is formed, for example, by a metal such as SUS304. The cross-section of the wire 31b of the closely wound portion 32 is, for example, rectangular, as shown in FIG. 2 and FIG. 3A. In this case, the four corners of the wire 31b preferably have a slight chamfered portion. A diameter of the closely wound portion 32 is, for example, 10 mm, and a thickness of the wire 31b in the closely wound portion 32 is, for example, 0.3 mm. The cross-sections of the wires 31b of the closely wound portion 32 in the diametrical direction of the closely wound portion 32 have the same length.

As shown in FIG. 2 and FIG. 3A, the closely wound portion 32 is formed so that the wires 31b adjacent in the axial direction of the spiral tube portion 31 are brought into close contact with each other without space therebetween by the above-mentioned initial tension. That is, in the closely wound portion 32, the wires 31b are in contact with each other in the axial direction of the spiral tube portion 31.

As shown in FIG. 2, the sparsely wound portion 33 is formed so that the wires 31b are provided apart from each other in the axial direction of the spiral tube portion 31 to have space in the axial direction of the spiral tube portion 31. That is, in the sparsely wound portion 33, the wires 31b are not in contact with each other in the axial direction of the spiral tube portion 31.

As shown in FIG. 2, in the present embodiment, the sparsely wound portions 33 are provided in the distal end portion 31g including the distal end of the spiral tube portion 31 (the flexible tubular portion 25), and the proximal end portion 31h including the proximal end of the spiral tube portion 31 (the flexible tubular portion 25), as described above. One sparsely wound portion 33a provided at the distal end is coupled to the bending portion 23, and the other sparsely wound portion 33b provided at the proximal end is coupled to the main body portion 61.

Figure 5A:
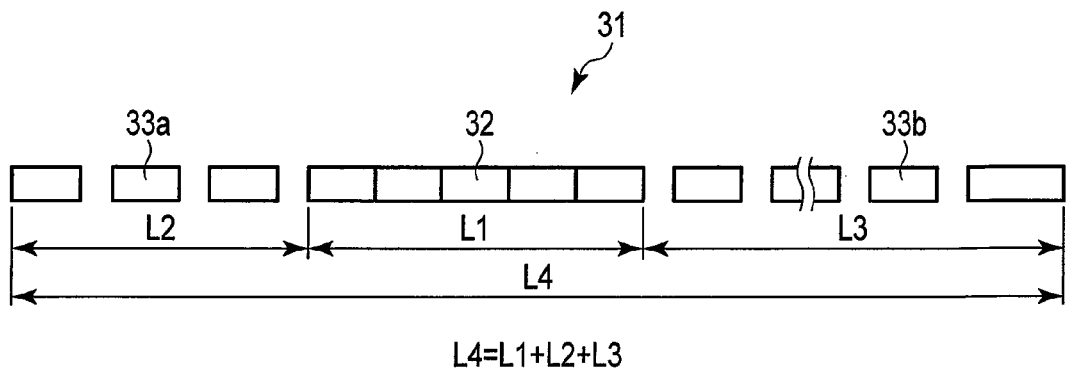
FIG. 5A is a diagram showing the relation between the length of the spiral tube portion, the length of a sparsely wound portion, and the length of the closely wound portion in a straight state.

Here, $L4=L1+L2+L3$  Equation (1)

wherein in the axial direction of the straight spiral tube portion 31, the length of the central axis of the closely wound portion 32 is L1, the length of the central axis of the one sparsely wound portion 33a is L2, the length of the central axis of the other sparsely wound portion 33b is L3, and the length of the central axis of the spiral tube portion 31 is L4, as shown in FIG. 5A.

In general, the length of the central axis of the outer tube 51 is invariable and remains the same whether the outer tube 51 is straight or bent. Therefore, the length of the central axis of the spiral tube portion 31 covered by the outer tube 51 also needs to be invariable and remain the same whether the spiral tube portion 31 is straight or bent.

Figure 5B:
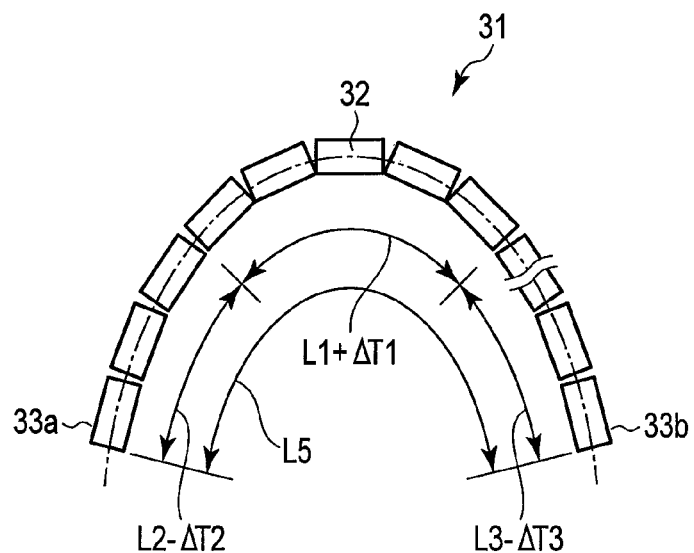
FIG. 5B is a diagram showing the relation between the length of the spiral tube portion, the length of the sparsely wound portion, and the length of the closely wound portion in a bent state.

As shown in FIG. 5B, if the spiral tube portion 31 is bent, the wires 31b provided on the central axis of the closely wound portion 32 are farther from each other than when the closely wound portion 32 is straight. Accordingly, the length of the central axis of the closely wound portion 32 increases $\Delta T1$. That is, when the spiral tube portion 31 is bent, the length of the central axis of the closely wound portion 32 is $L1+\Delta T1$.

If the condition remains the same, the length of the central axis of the spiral tube portion 31 varies by $\Delta T1$ between the straight and bent states of the spiral tube portion 31. However, in the present embodiment, the sparsely wound portions 33 are provided.

As shown in FIG. 5B, when the spiral tube portion 31 is bent, the wires 31b provided on the central axis of the one sparsely wound portion 33a are closer to each other than when the one sparsely wound portion 33a is straight. In other words, in the one sparsely wound portion 33a, the space between the wires 31b is smaller. Thus, the length of the central axis of the one sparsely wound portion 33a is $\Delta T2$ smaller than when the one sparsely wound portion 33a is straight. That is, when the spiral tube portion 31 is bent, the length of the central axis of the one sparsely wound portion 33a is $L2-\Delta T2$.

As shown in FIG. 5B, when the spiral tube portion 31 is bent, the wires 31b of the sparsely wound portion 33 provided on the central axis of the other sparsely wound portion 33b are closer to each other than when the other sparsely wound portion 33b is straight. In other words, in the other sparsely wound portion 33b, the space between the wires 31b is smaller. Thus, the length of the central axis of the other sparsely wound portion 33b is $\Delta T3$ smaller than when the other sparsely wound portion 33b is straight. That is, when the spiral tube portion 31 is bent, the length of the central axis of the other sparsely wound portion 33b is L3−ΔT3.

Here, $$L5 = L1 + \Delta T1 + L2 - \Delta T2 + L3 - \Delta T3 \quad \text{Equation (2)}$$

wherein the length of the central axis of the bent spiral tube portion 31 is L5, as shown in FIG. 5B.

Here, as described above, the length of the central axis of the spiral tube portion 31 needs to be invariable and remain the same whether the spiral tube portion 31 is straight or bent. That is, it is necessary that $$L4 = L5 \quad \text{Equation (3)}.$$

If Equations (1) and (2) are substituted for Equation (3), L1+L2+L3=L1+ΔT1+L2−ΔT2+L3−ΔT3, so that $$\Delta T1 = \Delta T2 + \Delta T3 \quad \text{Equation (4)}.$$

To put Equation (4) in other words, the stretch amount of the closely wound portion 32=the contraction amount of the one sparsely wound portion 33a+the contraction amount of the other sparsely wound portion 33b.

Thus, the stretch amount of the closely wound portion 32 is equal to the total of the contraction amounts of the sparsely wound portions 33, and the sparsely wound portions 33 contract as much as the stretch amount of the closely wound portion 32. That is, the sparsely wound portion 33 absorbs the stretch of the central axis of the spiral tube portion 31 associated with the stretch of the central axis of the closely wound portion 32 in the axial direction of the spiral tube portion 31 when the flexible tubular portion 25 is bent. In other words, the sparsely wound portion 33 offsets the stretch of the central axis of the spiral tube portion 31. As a result, the sparsely wound portion 33 can smoothly bend the flexible tubular portion 25 so that the characteristics of the closely wound portion 32 are maintained.

[Mesh Tube Portion 41]

The mesh tube portion 41 is formed by, for example, a bundle of stainless steel wires woven into the shape of a circular tube. In the mesh tube portion 41, the wires are crossed and in the form of a lattice.

[Outer Tube 51]

The outer tube 51 is formed by a flexible resin material such as a rubber material into the shape of a circular tube to cover the outside of the mesh tube portion 41.

[Operation Method]

Now, an operation method according to the present embodiment is described.

As shown in FIG. 2, the spiral tube portion 31 has the closely wound portion 32 to which the initial tension is applied, and the sparsely wound portions 33. The flexible tubular portion 25 has such a spiral tube portion 31.

Thus, when the straight flexible tubular portion 25 is inserted into a body cavity, the flexible tubular portion 25 keeps straight without flexing even if a load equal to or less than the initial tension, that is, the load B is applied to the flexible tubular portion 25, as shown in FIG. 4. As a result, the flexing amount becomes 0, the operating force amount at the hand side is transmitted to the distal end portion (the distal end portion 31g of the spiral tube portion 31) side of the flexible tubular portion 25, and the flexible tubular portion 25 is more easily inserted into the body cavity. That is, the flexible tubular portion 25 can be kept straight under the load B and is inserted into the body cavity without flexing.

Even if load equal to or more than the initial tension and equal to or less than the load C1 is applied to the flexible tubular portion 25, the flexible tubular portion 25 flexes less than the flexible tubular portion having the spiral tube portion 131. Thus, the operating force amount at the hand side is transmitted to the distal end portion side of the flexible tubular portion 25 as compared to the flexible tubular portion having the spiral tube portion 131, and the flexible tubular portion 25 is more easily inserted into the body cavity.

When the flexible tubular portion 25 is inserted in the body cavity and flexes by the load equal to or more than the initial tension and equal to or less than the load C1, load (e.g., the load C2) equal to or more than the load C1 is additionally applied to the flexible tubular portion 25, so that the flexing flexible tubular portion 25 is flexed more than the flexible tubular portion having the spiral tube portion 131b, as shown in FIG. 4.

When the flexible tubular portion 25 is inserted in the body cavity and flexed by the load equal to or more than the initial tension and equal to or less than the load C2, a load equal to or more than the load C2 is additionally applied to the flexible tubular portion 25, so that the flexing flexible tubular portion 25 is flexed more than the flexible tubular portion having the spiral tube portion 131a, as shown in FIG. 4.

Thus, when the already flexing flexible tubular portion 25 is further flexed in the body cavity under the load equal to or more than the load C2, the flexible tubular portion 25 having the closely wound portion 32 does not apply strong tension to the intestines under the same load even if the flexible tubular portion 25 abuts on the flection of the large intestine, so that no burden is imposed on the patient. Moreover, the flexible tubular portion 25 having the closely wound portion 32 is flexed more than the flexible tubular portion having the spiral tube portion 131. At the same time, the flexible tubular portion 25 having the closely wound portion 32 is flexed by less load than the flexible tubular portion having the spiral tube portion 131 with the same flexing amount. In this way, the operation of the flexible tubular portion 25 is easier.

When the flexible tubular portion 25 is flexed, the sparsely wound portion 33 absorbs the stretch of the central axis of the spiral tube portion 31 associated with the stretch of the central axis of the closely wound portion 32 in the axial direction of the spiral tube portion 31. As a result, the flexible tubular portion 25 is smoothly flexed by the sparsely wound portion 33 so that the characteristics of the closely wound portion 32 are maintained.

[Advantageous Effects]

As described above, according to the present embodiment, the spiral tube portion 31 has the closely wound portion 32 to which the initial tension is applied. Thus, according to the present embodiment, the flexing amount of the flexible tubular portion 25 can be 0 or smaller even if a load is applied to the straight flexible tubular portion 25. If a load is further applied to the flexing flexible tubular portion 25, the flexing amount of the flexible tubular portion 25 can be greater.

According to the present embodiment, the straight or slightly flexing flexible tubular portion 25 can be easily inserted into the body cavity. Thus, according to the present embodiment, the operating force amount at the hand side can be positively and easily transmitted to the distal end portion side of the flexible tubular portion 25, and the flexible tubular portion 25 can be more easily inserted into the body cavity.

According to the present embodiment, the flexible tubular portion 25 does not need to strongly abut on the flection of the large intestine to increase the flexing amount. In the body cavity, strong tension is not applied to the intestines, and no burden is imposed on the patient. According to the present embodiment, the operation of the flexible tubular portion 25 can be easier.

According to the present embodiment, the initial tension is applied to the closely wound portion 32 when the closely wound portion 32 is formed. Thus, according to the present embodiment, the initial tension is not applied after the closely wound portion 32 and the flexible tubular portion 25 have been manufactured. Therefore, the time in the manufacture of the closely wound portion 32 and the flexible tubular portion 25 can be reduced.

According to the present embodiment, as shown in FIG. 5B, when the flexible tubular portion 25 is bent, the sparsely wound portion 33 absorbs the stretch of the central axis of the spiral tube portion 31 associated with the stretch of the central axis of the closely wound portion 32 in the axial direction of the spiral tube portion 31. Thus, according to the present embodiment, the flexible tubular portion 25 can be smoothly bent so that the characteristics of the closely wound portion 32 are maintained by the sparsely wound portion 33.

According to the present embodiment, the sparsely wound portion 33 is adjoined to the closely wound portion 32. Thus, according to the present embodiment, the stretch of the closely wound portion 32 can be immediately absorbed by the sparsely wound portion 33.

According to the present embodiment, as shown in FIG. 2, the sparsely wound portions 33 are provided in the distal end portion 31g including the distal end of the spiral tube portion 31 (the flexible tubular portion 25), and the proximal end portion 31h including the proximal end of the spiral tube portion 31 (the flexible tubular portion 25). Thus, according to the present embodiment, the influence of the stretch of the closely wound portion 32 on the bending portion 23 can be prevented by the one sparsely wound portion 33a, and the influence of the stretch of the closely wound portion 32 on the main body portion 61 can be prevented by the other sparsely wound portion 33b.

According to the present embodiment, as shown in FIG. 2, the sparsely wound portions 33 are provided in both ends of the closely wound portion 32. However, the positions of the sparsely wound portions 33 do not need to be limited thereto. The sparsely wound portion 33 has only to be provided at least at one end of the closely wound portion 32.

According to the present embodiment, as shown in FIG. 2, in the axial direction of the spiral tube portion 31, the spiral tube portion 31 has the sparsely wound portion 33a, the closely wound portion 32, and the sparsely wound portion 33b in order from the distal end portion 31g of the spiral tube portion 31 (the flexible tubular portion 25) to the proximal end portion 31h of the spiral tube portion 31 (the flexible tubular portion 25). However, the arrangement of the closely wound portion 32 and the sparsely wound portions 33 does not need to be limited thereto.

Figure 6A:
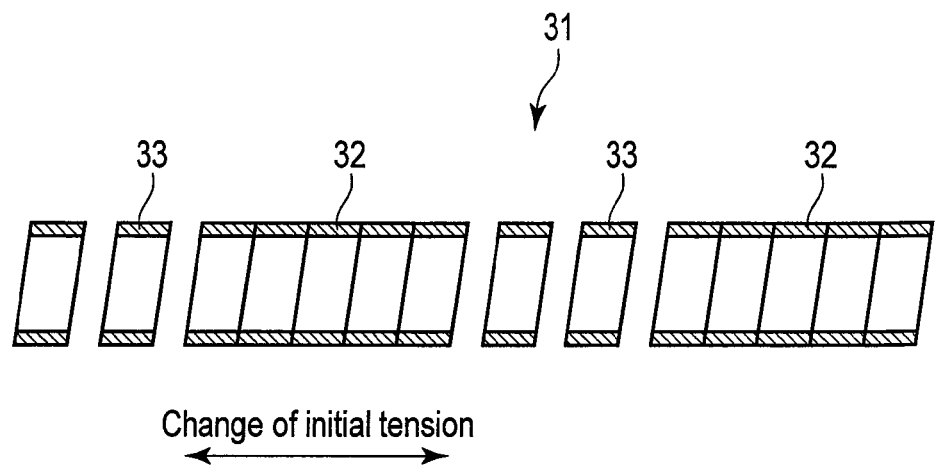
FIG. 6A is a diagram showing a first modification in the arrangement of the closely wound portion and the sparsely wound portion.

As in a first modification of the arrangement of the closely wound portions 32 and the sparsely wound portions 33 shown in FIG. 6A, the spiral tube portion 31 may have, for example, the sparsely wound portion 33, the closely wound portion 32, the sparsely wound portion 33, and the closely wound portion 32 in order from the distal end portion 31g of the spiral tube portion 31 (the flexible tubular portion 25) to the proximal end portion 31h of the spiral tube portion 31 (the flexible tubular portion 25) in the axial direction of the spiral tube portion 31.

Figure 6B:
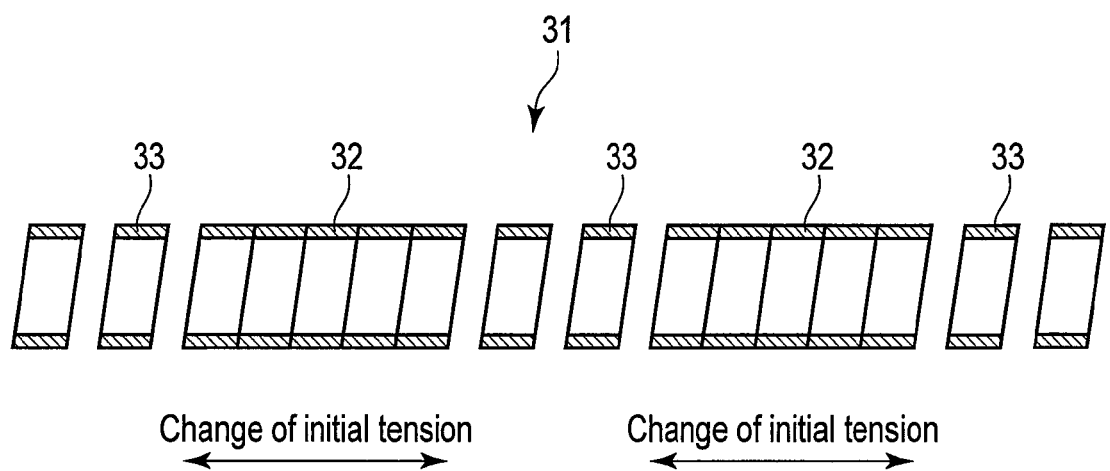
FIG. 6B is a diagram showing a second modification in the arrangement of the closely wound portion and the sparsely wound portions.

As in a second modification of the arrangement of the closely wound portions 32 and the sparsely wound portions 33 shown in FIG. 6B, the spiral tube portion 31 may have, for example, the sparsely wound portion 33, the closely wound portion 32, the sparsely wound portion 33, the closely wound portion 32, and the sparsely wound portion 33 in order from the distal end portion 31g of the spiral tube portion 31 (the flexible tubular portion 25) to the proximal end portion 31h of the spiral tube portion 31 (the flexible tubular portion 25) in the axial direction of the spiral tube portion 31.

Thus, the closely wound portion 32 and the sparsely wound portion 33 have only to be alternately provided along the axial direction of the spiral tube portion 31. In this case, the sparsely wound portions 33 and the closely wound portions 32 are not particularly limited in number if alternately provided. Thus, according to the present embodiment, the closely wound portions 32 are provided in a wide range. Therefore, the flexible tubular portion 25 can be more flexibly bent, and the bending degree of the flexible tubular portion 25 can be adjusted.

As shown in FIG. 2, the sparsely wound portions 33 are provided in the distal end portion 31g including the distal end of the spiral tube portion 31 (the flexible tubular portion 25), and the proximal end portion 31h including the proximal end of the spiral tube portion 31 (the flexible tubular portion 25). However, the sparsely wound portions 33 do not need to be limited thereto. The sparsely wound portion 33 has only to be provided at least at one of the distal end portion 31g of the spiral tube portion 31 and the proximal end portion 31h of the spiral tube portion 31. Thus, the flexible tubular portion 25 has the sparsely wound portion 33 provided at least at one of the distal end portion 31g and the proximal end portion 31h of the spiral tube portion 31.

The flexible tubular portion 25 according to the present embodiment has the spiral tube portion 31 (the closely wound portion 32 and the sparsely wound portion 33), the mesh tube portion 41, and the outer tube 51, and has a three-layer structure. However, the structure of the flexible tubular portion 25 does not need to be limited thereto. The flexible tubular portion 25 has only to have at least, for example, the closely wound portion 32 to the whole of which the initial tension is applied, and the sparsely wound portion 33.

According to the present embodiment, the initial tension is applied to the whole of the closely wound portion 32. However, the initial tension does not need to be limited thereto. The initial tension may be applied to at least a part of the closely wound portion 32. The spiral tube portion 31 may have the closely wound portion 32 to at least a part of which the initial tension is applied, and the sparsely wound portion 33. The flexible tubular portion 25 has only to have at least such a spiral tube portion 31.

According to the present embodiment, the initial tension is continuously applied from the distal end portion 32a to the proximal end portion 32b. However, the initial tension does not need to be limited thereto. For example, the initial tension may be applied to the distal end portion 32a and the proximal end portion 32b, and does not have to be applied to the part between the distal end portion 32a and the proximal end portion 32b. Thus, the initial tension may be discontinuously applied. In this case, each initial tension is, for example, substantially the same.

The magnitude of the initial tension according to the present embodiment may change in the axial direction of the closely wound portion 32. For example, the initial tension applied to the side of the proximal end portion 32b of the closely wound portion 32 is greater than the initial tension applied to the side of the distal end portion 32*a*. In this case, the initial tension is smaller from the side of the distal end portion 32*a* of the closely wound portion 32 to a desired part on the side of the proximal end portion 32*b* of the closely wound portion 32, and is greater from the desired part to the proximal end portion 32*b* of the closely wound portion 32. Alternatively, the initial tension may gradually increase continuously from the side of the distal end portion 32*a* toward the side of the proximal end portion 32*b*.

Thus, the side of the distal end portion 32*a* is formed as a soft portion, and the rigidity on the side of the distal end portion 32*a* is low. The side of the proximal end portion 32*b* is formed as a hard portion, and the rigidity on the side of the proximal end portion 32*b* is high.

Thus, according to the present embodiment, the side of the distal end portion 32*a* is formed as the soft portion. Consequently, the side of the distal end portion 32*a* can be inserted along the intestines without applying strong tension to the intestines even if the side of the distal end portion 32*a* abuts on the flection of the large intestine. The side of the distal end portion 32*a* can be easily inserted into the body cavity, and the burden on the patient can be reduced.

According to the present embodiment, the side of the proximal end portion 32*b* is formed as the hard portion. Consequently, even if the operating force amount at the hand side is applied to the flexible tubular portion 25, that is, even if the operator applies force (load) to the flexible tubular portion 25, the flexible tubular portion 25 can be prevented from being easily flexed, the operating force amount at the hand side can be easily transmitted to the distal end portion 32*a*, and the flexible tubular portion 25 can be easily inserted into the body cavity.

According to the present embodiment, the advantageous effects described above can be obtained as along as the initial tension is only applied to the side of the proximal end portion 32*b*. In this case, for example, when the initial tension is not applied to the distal end portion 32*a* and is applied to the side of the proximal end portion 32*b*, the magnitude of the initial tension applied to the side of the proximal end portion 32*b* may be uniform in the whole of the side of the proximal end portion 32*b*, or may gradually increase toward the proximal end portion 32*b*.

As described above, the initial tension may be discontinuously applied. In this case, the initial tension applied to the side of the distal end portion 32*a* is lower than the initial tension applied to the side of the proximal end portion 32*b*. Moreover, the magnitude of the initial tension applied to the side of the distal end portion 32*a* gradually increases toward the proximal end portion 32*b* as described above, and the initial tension applied to the side of the proximal end portion 32*b* gradually increases toward the proximal end portion 32*b* as described above. In this case, the highest initial tension applied to the side of the distal end portion 32*a* is, for example, lower than the lowest initial tension applied to the side of the proximal end portion 32*b*.

Thus, the magnitude of the initial tension is the same or varies in the axial direction of the closely wound portion 32. In other words, the respective closely wound portions 32 have uniform initial tension or different initial tensions. Thus, according to the present embodiment, the hardness or resilient force of the flexible tubular portion 25 can be freely adjusted to the use of the flexible tubular portion 25, and the operability of the flexible tubular portion 25 can be freely adjusted.

The above-mentioned change of the initial tension may be applied to one closely wound portion 32 as shown in FIG. 6A, or may be applied to more than one closely wound portion 32 as shown in FIG. 6B. When more than one closely wound portion 32 is provided, the initial tension applied to the closely wound portion 32 on the side of the distal end portion 31*g* may be the same as or different from the initial tension applied to the closely wound portion 32 on the side of the proximal end portion 31*h*. When the initial tension varies, the initial tension may gradually increase from the distal end portion 32*a* of the closely wound portion 32 on the side of the distal end portion 31*g* toward the proximal end portion 32*b* of the closely wound portion 32 on the side of the proximal end portion 31*h*. Thus, the application of the initial tension is not particularly limited as long as the initial tension is applied to at least a part of the closely wound portion 32.

Thus, according to the present embodiment, as shown in FIG. 2, the cross-sections of the wires 31*b* of the closely wound portion 32 have the same length in the axial direction of the closely wound portion 32, but the present invention does not need to be limited thereto. For example, the cross-sectional shape of the wire 31*b* of the closely wound portion 32 in the axial direction of the closely wound portion 32 may change in the axial direction of the closely wound portion 32. This change shows that, for example, at least one of the thickness of the wire 31*b* corresponding to the length of the diametrical direction of the wire 31*b* and the length corresponding to the width of the wire 31*b* changes in the axial direction of the closely wound portion 32. This change means that, for example, the width of the closely wound portion 32 provided on the side of the distal end portion 31*g* of the spiral tube portion 31 is shorter than the width of the closely wound portion 32 provided on the side of the proximal end portion 31*h* of the spiral tube portion 31. This change also means that, for example, in one closely wound portion 32, the width on the side of the distal end portion 31*g* is shorter than the width on the side of the proximal end portion 31*h*. Thus, according to the present embodiment, the flexible tubular portion 25 can be more flexibly bent, and the bending degree of the flexible tubular portion 25 can be adjusted. Therefore, in the cross-section of the wire 31*b* of the closely wound portion 32, the length of in the cross-section in the axial direction of the closely wound portion 32 may be the same or vary.

Figure 6C:
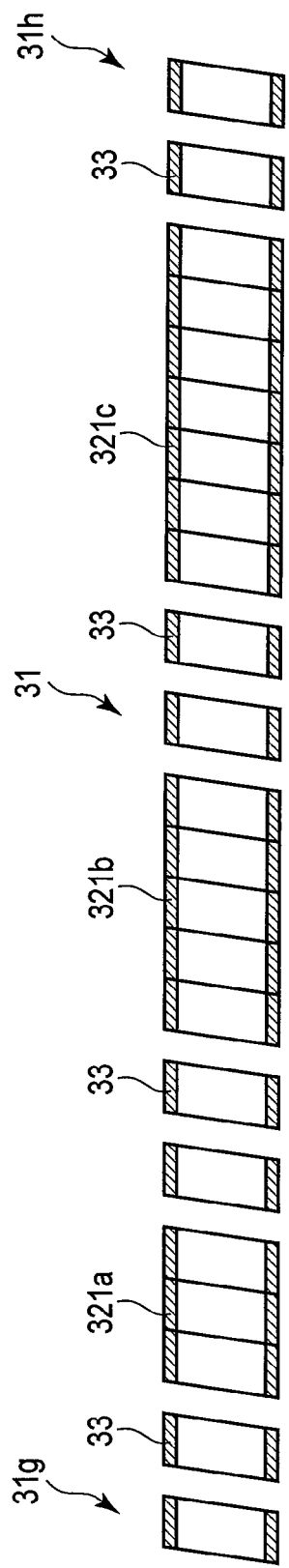
FIG. 6C is a diagram showing the change in the number of turns of the closely wound portion.

According to the present embodiment, the number of turns of the closely wound portion 32 may change. For example, as shown in FIG. 6C, the number of turns of a closely wound portion 321*a* provided on the side of the distal end portion 31*g* of the spiral tube portion 31 is 3, the number of turns of a closely wound portion 321*b* provided closer to the side of the proximal end portion 31*h* of the spiral tube portion 31 than the closely wound portion 321*a* is 5, and the number of turns of a closely wound portion 321*c* provided closer to the side of the proximal end portion 31*h* of the spiral tube portion 31 than the closely wound portion 321*b* is 7. The change of the number of turns is substantially similar to the above-mentioned change of the initial tension.

Thus, according to the present embodiment, the flexibility of the spiral tube portion 31 can be changed, the degree of freedom of flexibility can be improved, and the flexible tubular portion 25 having diverse flexibilities can be provided.

Although the number of turns of the closely wound portion 32 changes according to the present embodiment, the present invention does not need to be limited thereto. The number of turns of the sparsely wound portion 33 may change. Thus, the number of turns of at least one of the closely wound portion 32 and the sparsely wound portion 33 may change in the axial direction.

According to the present embodiment, the present invention does not need to be limited to the above as long as the flexibility of the spiral tube portion 31 can be changed. For example, the outside diameter of the closely wound portion 32 may change. For example, the outside diameter of the closely wound portion 321b is greater than the outside diameter of the closely wound portion 321a, and the outside diameter of the closely wound portion 321c is greater than the outside diameter of the closely wound portion 321b. For example, the outside diameter of the closely wound portion 321a may change in such a way as to increase from the distal end portion 31g toward the proximal end portion 31h in the axial direction of the spiral tube portion 31. The variation of the outside diameter is substantially similar to the above-mentioned change of the initial tension.

Although the outside diameter of the closely wound portion 32 changes according to the present embodiment, the present invention does not need to be limited thereto, and the outside diameter of the sparsely wound portion 33 may change. Thus, the outside diameter of at least one of the closely wound portion 32 and the sparsely wound portion 33 may change in the axial direction of the spiral tube portion 31.

Figure 7A:
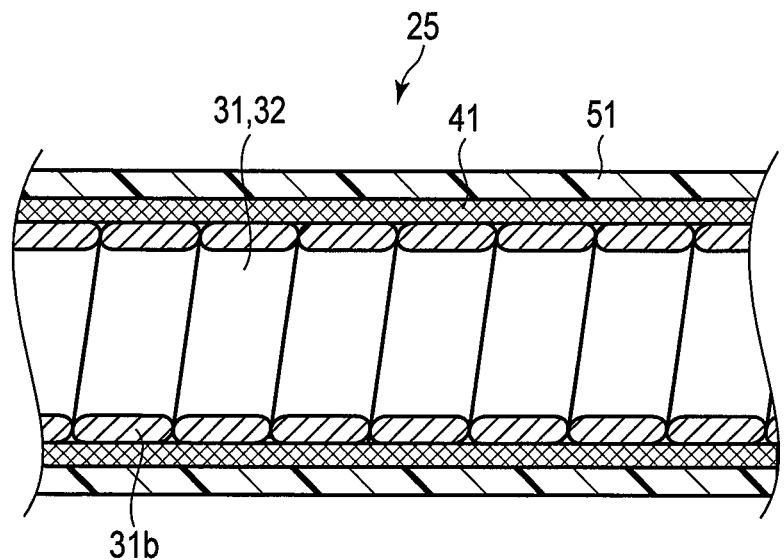
FIG. 7A is a diagram showing a first modification of the sectional shape of a wire in the closely wound portion.

According to the present embodiment, the cross-section of the wire 31b of the closely wound portion 32 may have an oval shape as a first modification of the cross-sectional shape of the wire 31b of the closely wound portion 32 shown in FIG. 7A. Thus, in the present modification, the section of the wire 31b is R-shaped. Therefore, the winding angle at which the wire 31b is spirally wound can be obtuse as compared to the case where the section is rectangular. Thus, according to the present embodiment, a higher initial tension can be applied to the closely wound portion 32. Moreover, in the present modification, the cross-section has the oval shape, so that the wires 31b are in point contact with each other, and the area of contact between the wires 31b is smaller. Thus, in the present modification, the friction between the wires 31b is reduced, and the closely wound portion 32 can be smoothly bent.

Figure 7B:
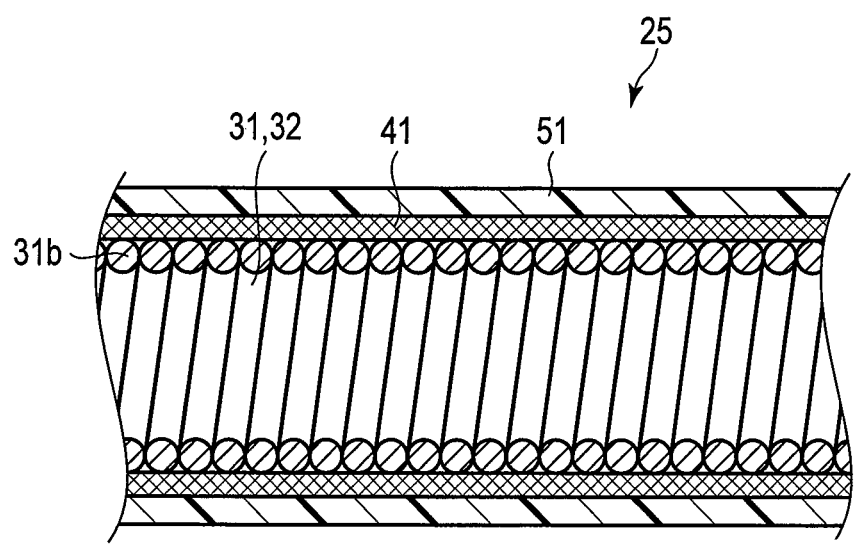
FIG. 7B is a diagram showing a second modification of the sectional shape of the wire in the closely wound portion.

According to the present embodiment, as in a second modification of the cross-sectional shape of the wire 31b of the closely wound portion 32 shown in FIG. 7B, the cross-section of the wire 31b of the closely wound portion 32 may have a circular shape. Thus, in the present modification, the cross-section of the wire 31b has no edge, so that it is possible to prevent the wires 31b from running on each other in the diametrical direction when the wires 31b are curved into the R-shape having a low curvature.

Figure 7C:
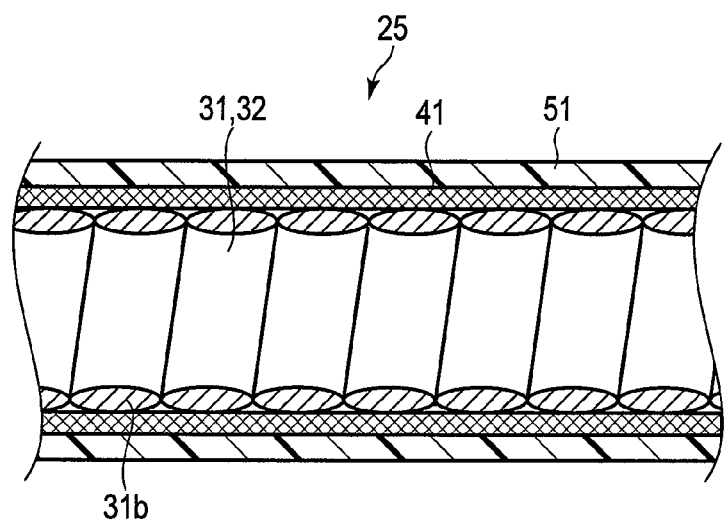
FIG. 7C is a diagram showing a third modification of the sectional shape of the wire in the closely wound portion.

According to the present embodiment, as in a third modification of the sectional shape of the wire 31b of the closely wound portion 32 shown in FIG. 7C, the cross-section of the wire 31b of the closely wound portion 32 may have an elliptic shape. Thus, in the present modification, it is possible to improve the resistance of the wire 31b to collapse without increasing the size of the wire 31b in its diametrical direction.

In view of the above, the cross-section of the wire 31b of the closely wound portion 32 may have, for example, at least one of the rectangular shape, the oval shape, the circular shape, and the elliptic shape.

In this case, when the section of the wire 31b has one of the rectangular shape, the oval shape, and the elliptic shape, the above-mentioned length of the cross-section in the axial direction of the closely wound portion 32 means at least one of the length corresponding to the thickness of the wire 31b and the length corresponding to, for example, the width of the wire 31b in the closely wound portion 32 as described above. When the cross-section of the wire 31b has the circular shape, the above-mentioned length of the section in the axial direction of the closely wound portion 32 means, for example, the diameter of the wire 31b.

The endoscope 1 may be used for medical purposes or industrial purposes.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An insertion portion of an endoscope, the insertion portion comprising:
   a flexible tube having a distal end and a proximal end as defined with respect to a longitudinal axis of the flexible tube, the flexible tube being insertable into a body cavity along a longitudinal axial direction;
   a bending portion extending from a distal end of the flexible tube, the bending portion being bendable in a direction different from the longitudinal axial direction in accordance with actuation of an operation knob of the endoscope; and
   a spiral tube disposed in the flexible tube, the spiral tube comprising:
      a sparsely wound portion in which a wire is spirally wound with adjacent turns of the wire being spaced apart from each other along the longitudinal axial direction; and
      a closely wound portion in which the wire is spirally wound with adjacent turns of the wire being in close contact with each other along the longitudinal axial direction;
   wherein the sparsely wound portion is provided at respective ends of the closely wound portion and terminates at the distal and proximal ends of the flexible tube, and
   wherein in the closely wound portion, in which the adjacent turns of the wire are in close contact with each other along the longitudinal axial direction, the wire is under an initial tension that is a force which keeps the adjacent turns of the wire in close contact in the longitudinal axial direction against a load smaller than or equal to a predetermined value applied along a radial direction of the flexible tube.

2. The insertion portion according to claim 1, wherein the closely wound portion and the sparsely wound portion are alternately provided along the longitudinal axial direction.

3. The insertion portion according to claim 2, wherein a number of turns of at least one of the closely wound portion and the sparsely wound portion is configured to change along the longitudinal axial direction.

4. The insertion portion according to claim 1, wherein an outside diameter of at least one of the closely wound portion and the sparsely wound portion is configured to change along the longitudinal axial direction.

5. The insertion portion according to claim 1, wherein a magnitude of the initial tension is configured to change along the longitudinal axial direction.

6. The insertion portion according to claim 1, wherein a cross-sectional shape of the wire of the closely wound portion in an axial direction of the closely wound portion is configured to change in the longitudinal axial direction.

7. The insertion portion according to claim 1, wherein a cross-sectional shape of the wire of the closely wound portion is at least one of a rectangular shape, an oval shape, a circular shape, and an elliptic shape.

8. An endoscope comprising the insertion portion according to claim 1.

9. The insertion portion according to claim 1, wherein when the load is applied to the closely wound portion and the sparsely wound portion along the radial direction of the flexible tube, a flexing amount of the closely wound portion being flexed under the load is smaller than a flexing amount of the sparsely wound portion being flexed under the load.

* * * * *